US006214377B1

(12) United States Patent
Dittgen et al.

(10) Patent No.: US 6,214,377 B1
(45) Date of Patent: *Apr. 10, 2001

(54) MELATONIN FOR THE PRODUCTION OF A PERORAL PULSATILE FORM OF MEDICATION

(75) Inventors: Michael Dittgen, Apolda; Sabine Fricke, Jena; Thomas Gräser, Erfurt; Hermann Osterwald, Bovenden; Michael Oettel, Jena; Theodor Hermann Lippert, Tü bingen, all of (DE)

(73) Assignee: Jenapharm GmbH, Jena (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/567,294

(22) Filed: Dec. 5, 1995

(30) Foreign Application Priority Data

Dec. 5, 1994 (DE) .................................................. 44 43 175

(51) Int. Cl.⁷ .............................. A61K 9/58; A61K 9/20; A61K 9/14; A61K 9/16
(52) U.S. Cl. ......................... 424/462; 424/464; 424/482; 424/497; 424/489
(58) Field of Search .................................. 424/464, 462, 424/482, 497, 489

(56) References Cited

U.S. PATENT DOCUMENTS 4,652,441 * 3/1987 Okada et al. ........................ 424/497
5,498,423 * 3/1996 Zisapel ................................. 424/464
5,707,652 * 1/1998 Lewy et al. .......................... 424/457

FOREIGN PATENT DOCUMENTS

| PCT/US90/06505 | 11/1990 | (WO) | .............................. A61K/9/20 |
| PCT/US94/08365 | 7/1994 | (WO) | .............................. A61K/31/40 |

OTHER PUBLICATIONS

Remington's Pharmaceutical Science, Fifteenth Edition, John E. Hoover, Managing Managing Editor, Mack Publishing Company, 1975, pp. 1598 to 1605.

Boem–Jin Lee et al.; "Development and Characterization of an Oral Controlled–Release Delivery System for Melatonin": Drug Development and Industrial Pharmacy 22; pp. 269–276; 1996.

* cited by examiner

Primary Examiner—Thurman K. Page
Assistant Examiner—A. Pulliam
(74) Attorney, Agent, or Firm—Horst M. Kasper

(57) ABSTRACT

The use of melatonin for the production of peroral pulsatile forms of medications assures the safeguard of an effective level of the medical substance of melatonin in the blood, and which realize a relatively short invasion phase with a controlled delivery in comparison to conventional forms of medication containing melatonin, and which simultaneously exclude the known side effects. A control of the delivery of the melatonin is effected which is associated with the precise adaptation to the illness episodes or the pain attacks of certain illnesses, which can be treated prophylactically and therapeutically with the active agent melatonin.

24 Claims, 3 Drawing Sheets

MELATONIN FOR THE PRODUCTION OF A PERORAL PULSATILE FORM OF MEDICATION

BACKGROUND OF THE INVENTION

1. Field of the Invention

Figure 1:
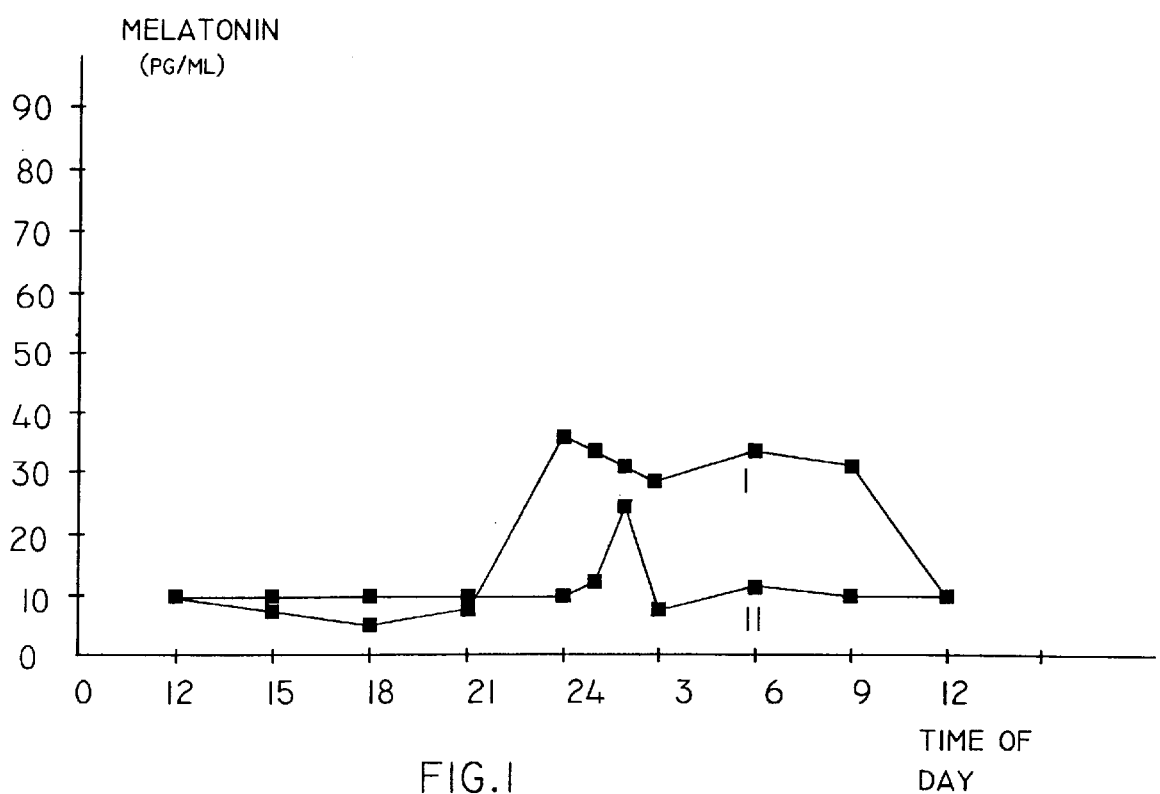

The invention relates to a method of using melatonin for the production of peroral pulsatile forms of medication for safeguarding an effective blood level of the medical substance melatonin, which pulsatile forms realize a controlled delivery within a relatively short invasion phase in contrast to conventional forms of medication containing melatonin and which pulsatile forms exclude at the same time the known side effects.

2. Brief Description of the Background of the Invention Including Prior Art

The term "pulsatile forms of medication" is synonymous with the term "regulated or modulated delivery systems" and designates according to Peppas (N. A. Peppas, Preface in R. Gurny; H. E. Junginger; N. A. Peppas (Eds.) Pulsatile Drug Delivery, Current Applications and Future Trends, 1 Ed., page 5–5, Wiss. Verlagsges., Stuttgart 1993) a delivery system which is capable of delivering the contained medical agent in prescribed intervals in response to the situation in the surrounding liquid or based on an external stimulus.

The preferred field of application of pulsatile forms of medication are illnesses such as ischaemia, asthma, arthritis, sleep disorders, Parkinson's Syndrome, incontinence, aids, and states of pain (H. E. Junginger, Oral Applications of Pulsatile Drug Delivery in R. Gurny; H. E. Junginger; N. A. Peppas (Eds.) Pulsatile Drug Delivery, Current Applications and Future Trends, Ed. 1, pages 113–134, Wiss. Verlagsges., Stuttgart 1993). These illnesses or states of pain are subjected to time variations such that they can be treated best with forms of medication, which are adapted with the intermittent (pulsatile) release of the medical agents to the occurrence of episodes of the illness or of attacks of the pain.

Typical pulsatile forms of medication deliver the contained medical agent in one step (one pulse system) or in two steps (bimodal, double pulse system).

In addition, however also more complicated systems and mixed systems have been described, which can possibly deliver the medical substance melatonin in several steps.

Junginger (H. E. Junginger, Oral Applications of Pulsatile Drug Delivery in R. Gurny; H. E. Junginger; N. A. Peppas (Eds.) Pulsatile Drug Delivery, Current Applications and Future Trends, Ed. 1., pages 1 13–134, Wiss. Verlagsges., Stuttgart 1993) gives examples for pulsatile forms of medication and recites in particular:

coated tablets, pellets or microballs, osmotic systems, special capsules, time-controlled explosion systems, special layer tablets.

The methods known up to now for the production of a pulsatile form of medication are thus all associated with the substantial disadvantage that special lines of production as well as expensive devices or a costly precision production are necessary.

Melatonin (N-acetyl-5-methoxy-triptamine) itself is a hormone of the pineal gland and is secreted predominantly during the night hours. Since melatonin interacts in many ways in the different regulating circles in the human body and exerts different physiological and pharmacological effects, various experiments and results are known from the professional and patent literature relating to the different directions of effectiveness of the melatonin.

For example, FIG. 1 according to K. A. Stokkan et al.; J. Pineal Res. 16, 33–36, 1994, and B. L. Parry et al.: Arch. Gen. Psychiatry 47, 1139–1146, 1990, shows in its graphical representation of the blood level curve (concentration of the melatonin versus time) the physiological course of the circadian delivery of melatonin in a healthy person (I) and in an ill person (II).

It can be recognized that a relatively steep rise of the surging on of the endogenous melatonin is recorded in a healthy human being, whereby a quick falling-asleep phase is characterized; then, there occurs a relatively flat drop of the endogenous melatonin level in the blood, which safeguards the sleep-through phase, the maximum of the level of endogenous melatonin in the blood ($C_{max-e}$) occurs belatedly in an ill person and there is associated therewith a delay of the falling-asleep phase; then, there occurs a steep drop of the level of endogenous melatonin in the blood, i.e. a wake-up phase occurs, and the sleep-through phase is not safeguarded.

Melatonin was applied up to now for example in an intranasal, intraocular, intravaginal, or rectal form of preparation. The circumvention of the liver passage was thereby in fact realized, however, the disadvantage of these solutions resides in that a follow-up administration is necessary at short-time intervals of from 1 to 2 hours. The cause for this according to L. Wetterberg et al.: A Simplified Radioimmunoassay for Melatonin and its Application to Biological Fluids, Preliminary Observations on the Half-Line of Plasma Melatonin in Man, Clinica Chimica Acta 86: 169–177, 1978; M. Aldhous et al.: Plasma Concentration of Melatonin in Man Following Oral Absorption of Different Preparations, Br. J. Clin. Pharmac. 19: 517, 521, 1985, and C. Mallo et al.: Eur. J. Clin. Pharmacol. 38: 297–301, 1990, is associated with the extremely short half-life period of melatonin in the human body which amounts to about 30 minutes.

Both the production as well as the application possibilities of adhesive carrier systems, i.e. transmucosal patches, are described in the Printed Patent document WO 91/06290. It is pointed out that these carrier systems are particularly well suited to produce and/or to maintain therapeutically an effective blood level. According to an embodiment, the use of the patches for the administration of melatonin is described. The transdermal application with various plasters does not bring satisfying results according to R. V. Short: Melatonin. Hormone of Darkness. Br. Med. J. 307: 952–953, 1993, since the melatonin rise in the serum is very flat and since no clear and abrupt drop can be proven after removal of the plaster.

Further known applications of melatonin are performed orally, in the form of tablets, of dragées, or of hard gelatin capsules.

According to investigations, after an oral administration of melatonin, there result extremely high interindividual differences with respect to the resorption of the melatonin from the gastro-intestinal tract as well as initially extremely overshooting melatonin levels in the blood as well as a poorly controllable kinetic of the active agent in case of a repeated application, compare F. Waldhauser et al.: Sleep Laboratory Investigations on Hypnotic Properties of Melatonin, Psychopharmacology 100: 222–226, 1990, and A. Vermeulen: The Male Climacterium, Ann. Med. 25: 531–534, 1993.

In the case of peroral administrations based on melatonin, the first-pass mechanism forces an administration which is overdone in an unphysiological overdose, compare E. A. Lane et al.: Pharmacokinetics of Melatonin in Man: First Pass Hepatic Metabolism. J. Clin. Endocrinol. Metab. 61: 1214–1216, 1985. Increased spasmogenic situations, confusion, and sleeplessness are thereby caused according to investigations, compare F. Waldhauser et al.: Sleep Laboratory Investigations on Hypnotic Properties of Melatonin, Psychopharmacology 100: 222–226, 1990, and A. Vermeulen: The Male Climacterium, Ann. Med. 25: 531–534, 1993.

An oral form of medication, containing among others a melatonin, is taught in the Printed Patent document WO 95/03043, which realizes the regulation of the physiological course of the circadian delivery of melatonin in older patients, in particular in patients suffering from Alzheimer's disease.

The disadvantage of this solution comprises that the application of the form of medication should occur either 4 to 17 hours prior to the time of the endogenous delivery of melatonin or 6 to 19 hours prior to the normal sleep phase.

Figure 2:
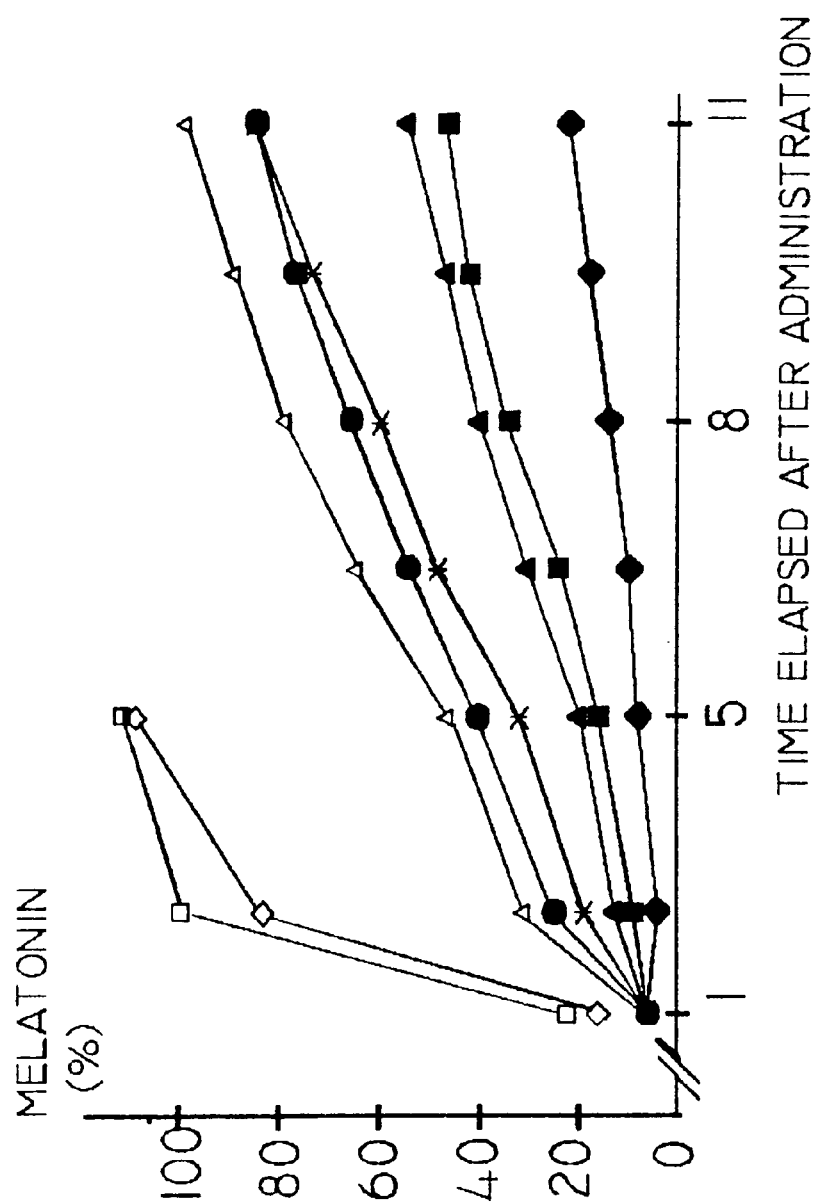

This requires a very original and willful rhythm of ingestion, which is very hard to realize in particular in case of patients which are suffering from Alzheimer's disease. The above recited rhythm of ingestion allows to suspect a very low initial level of melatonin in the blood, i.e. blood level concentration, which occurs immediately upon the administration of the medical agent, and a relatively long invasion phase, i.e. the phase from the time of application of the medical agent to the appearance of the medical agent at the location of application. The associated drawing, FIG. 2, is not in concurrence with the rhythm of administration shown in the recited printed patent document.

The European Printed Patent Document EP 0,518,468 described an oral or, respectively, peroral form of medication containing melatonin, which also regulates the physiological course of the circadian melatonin delivery. It is a disadvantage in this solution that the maximum level of melatonin in the blood, i.e. melatonin level maximum $C_{max}$ in the blood, occurs only after more than two hours and thus the invasion phase, which is in the present instance to be equalled to the occurrence of the falling-asleep phase or, respectively, the occurrence of a pain-relieving effect, is larger than two hours, the time duration of the overall melatonin delivery amounts to about ten hours, and a delayed wake-up phase of about four hours with the corresponding side effects such as, for example, confusion and the like are noted.

SUMMARY OF THE INVENTION

1. Purposes of the Invention

It is an object of the invention to develop peroral pulsatile forms of medication containing melatonin for the safeguarding of an effective level of the medical agent melatonin in the blood which peroral pulsatile forms, as compared to conventional forms of medication, realizes a controlled delivery of the medical agent melatonin during an invasion phase of less than two hours, and which peroral pulsatile forms avoid the known side effects resulting from the application of melatonin.

These and other objects and advantages of the present invention will become evident from the description which follows.

2. Brief Description of the Invention

The present invention provides for the use of melatonin the for production of peroral pulsatile forms of medication for safeguarding effective blood values of medical substances wherein an invasion phase of less than two hours is employed.

It has been shown to be particularly advantageous to provide the peroral pulsatile form of medication containing melatonin, where melatonin is incorporated in pharmaceutically compatible carrier substances having different dielectric constants. These carrier substances containing the active ingredient are mixed in a ratio corresponding to the required delivery of the active ingredient. The resulting mixtures of the carrier substances containing the active ingredient are formed into a pulsatile form of medication of melatonin, wherein an invasion phase of less than 2 hours is obtained.

Furthermore, by way of simplification of the production based on less apparatus expenditure, there is made possible a saving of special coating processes and furthermore a high-cost precision production is avoided. The pulsatile form of medication can be a capsule.

The novel features which are considered as characteristic for the invention are set forth in the appended claims. The invention itself, however, both as to its method of operation, its products and physical requirements, together with additional objects and advantages thereof, will be best understood from the following description of specific embodiments and examples.

DESCRIPTION OF INVENTION AND PREFERRED EMBODIMENT

In accordance with the present invention, peroral pulsatile forms of medication containing melatonin are produced for safeguarding effective blood values of melatonin, wherein the administered melatonin exhibits an invasion phase duration of less than two hours.

Melatonin is mixed with different carrier materials, wherein the carrier materials show different speeds of releasing the melatonin associated therewith. There are carriers with quick release of melatonin and carriers with slow release of melatonin. A carrier effecting a quick release of melatonin is a dispersion of melatonin in peanut oil. A carrier effecting a slow release of melatonin is collagen having embedded melatonin and formed in microballs having a diameter of from about 30 to 100 micrometers. It has been found to be particularly advantageous to provide the peroral pulsatile form of medication containing melatonin, where melatonin is incorporated in pharmaceutically compatible carrier substances having different dielectric constants. These carrier substances having different dielectric constants are characterized by concurrent differences in the polarity of the respective substances, i.e. they are polar substances or apolar substances. Particular preferred carrier substances are furnished by glycol esters of alkane acids, by glycol esters of alkene acids, by glycerol esters of alkane acids, by glycerol esters of alkene acids, by polyalcohols, by peptides and mixtures thereof.

These carrier substances containing the active ingredient are mixed in a ratio corresponding to the required delivery of the active ingredient. The resulting mixtures of the carrier substances containing the active ingredient are formed into a pulsatile form of medication of melatonin, wherein an invasion phase of less than 2 hours or alternatively of a longer time period as desired are obtained.

The concentration of the melatonin in the carrier material can be from about 4 to 10 percent by weight of the resulting mixture and is preferably from about 5 to 8 percent by weight of the resulting mixture.

The medication is then manufactured into a suitable form for use by a patient. Any form suitable for delivery of a pulsatile agent is suitable such as the forms of coated tablets, pellets or microballs, osmotic systems, special capsules, time-controlled explosion systems, and special layer tablets. A preferred pulsatile form of medication to be administered is a capsule. Manufacturing methods for capsules are for example described in Remington's Pharmaceutical Sciences, Fifteenth Edition, John E. Hoover, Managing Editor, Mack Publishing Company, 1975, pages 1598 to 1605.

Figure 3:
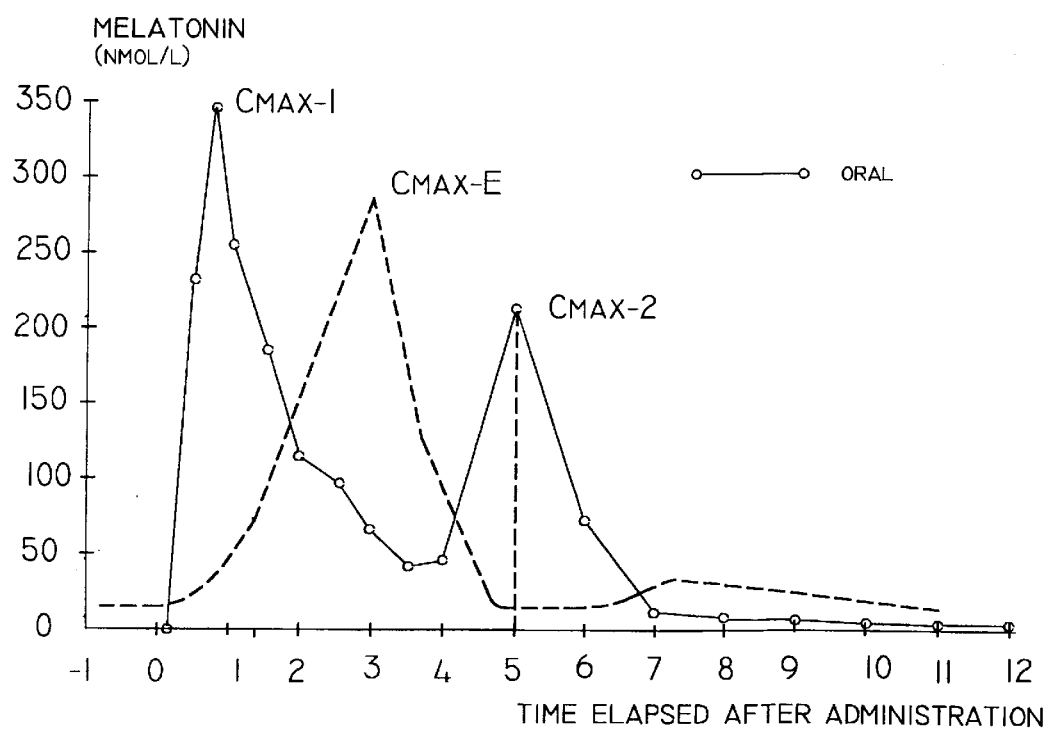

The amount of melatonin administered is generally an amount effective to achieve relief for the patient from the episodes of illnesses and from the attacks of pain recited above. The amount will be such that it leads to a level of melatonin in the blood of a patient which is from about 0.2 to 10 times and preferably of from about 0.5 to 2 times the level of melatonin in the blood to be expected in a healthy person under comparable circumstances. As shown in FIG. 3, such levels of melatonin in the blood can be in a range of from about 50 to 500 nmole per liter of blood and are preferably in a range of from about 100 to 300 nmole per liter of blood.

Preferably, medication such as tablets or caplets contain from about 1 to 20 milligrams total of melatonin and more preferably from about 2 to 5 milligrams total of melatonin. Preferably, a composition having a first carrier is present in an amount of more than 10% of the total of melatonin and a composition having a second carrier in an amount of less than 90% of the total amount of melatonin. More preferably, the composition having the first carrier is present in an amount of more than 20% of the total melatonin and the composition having the second carrier is present in an amount of less than 80% of the total amount of melatonin.

The production of the pulsatile form of medication according to the present invention dispenses of special coating processes, simplifies the steps involved in the production, bases itself on a less expensive type of apparatus, and avoids a high-cost production.

The present invention does not require an observance of specific production parameters such as of a thickness of a coating, of a release opening and/or of a precision coating, of properties of a hydrogel, of a precision dimensioning of a gel, and of a possible aging of a gel, of an exact tuning between an osmotic core material and an outer coating or of a precision of a pressing and the accuracy of the generated layer thickness.

EXAMPLE 1

For purposes of simplicity, only two-pulse systems are shown in this example.

The mixtures of carrying excipient and effective agent are shown in the following table and designated as composition 1 and composition 2.

Capsules with Melatonin

| Substance | Composition 1 | Composition 2 |
|---|---|---|
| Melatonin | 5.0 mg | 1.5 mg |
| Collagen | — | 25.0 mg |
| Dispersing Agent | 0.2 mg | — |
| Conservation Agent | — | 0.2 mg |
| Peanut Oil | 68.1 mg | — |

Production

The amount of melatonin (pulse 2) given in the composition 2 is embedded in a micronized form in balls of collagen having a diameter of 50 $\mu$m. The balls of collagen are dispersed jointly with the melatonin (pulse 1) in peanut oil in the amounts given in composition 1.

Delivery of the Active Agent

The delivery of the active agent was investigated in vitro as follows:

| Apparatus | according to DAB, "Deutsches Arzneibuch", 10th Edition, "Versuch" | 5.4 |
|---|---|---|
| | stirring speed | 300 rpm ± 2 rpm |
| | temperature | 37° C. + 1° C. |
| | volume of medium | 1000 ml |
| | medium | water, 3% SDS (sodium lauryl-sulfate, sodium dodecylsulfate) |

Result

Based on the variation of the ratio of melatonin in the composition 1 and the composition 2 (A1, A2), there are received in vitro release profiles, as shown in FIG. 2, which provide for a control of the melatonin release of 90% within a short time period of two hours, i.e. first arrival at the site of effect, and a control of the entire melatonin release of 100% within four hours.

It is known in the art that, based on the recited variation of the ratio of the active agent in the composition 1 and the composition 2, there is provided a control of the delivery of the active agent and thereby an accurate adaptation to the illness episodes or pain attacks of certain illnesses can be performed. In particular, according to FIG. 2 the ratio of the weight of the employed composition 1 relative to the weight of the employed composition 2 is changed. The contents of composition 1 in melatonin by weight is slightly higher than that of composition 2 by weight.

FIG. 3 shows the results of a pharmacological investigation of the blood level after application of a peroral pulsatile form of medication containing melatonin.

The maximum blood levels $C_{max-1}$ and $C_{max-2}$ describe in this case the respective highest concentration of the melatonin after the pulsed administration of the medical substance melatonin in two pulses. $C_{max-e}$ describes the maximum level of melatonin in the blood after the surging of the endogenous melatonin in the blood.

It can be recognized that the physiological course of the delivery of the melatonin after peroral pulsatile application occurs based on the following steps:

After an about 0.5 hour-long invasion phase, the first maximum level of melatonin $C_{max-1}$ in the blood is reached; a quick falling-asleep phase is shown.

A conscious phase for the surging up of the endogenous melatonin $C_{max-e}$ is observed; no overdose does occur with already recited side effects.

The second pulse of melatonin effects a second maximum level of melatonin $C_{max-2}$ in the blood, which second maximum level specifies the sleeping-through phase; the wake-up phase occurring in case of the circadian delivery of melatonin in ill persons is compensated by a sleep-through phase.

The wake-up phase in the case of a pulsatile application is a non-delayed one, which extends over two hours, and which avoids a hangover, i.e. a tiredness after waking up.

The recited physiological course of the delivery of the melatonin, effected by the application of a peroral pulsatile form of medication, for human beings affected with sleep disorders, can analogously be transferred to the control of the delivery of active agents of melatonin and, associated therewith, to a precise adaptation to illness episodes or pain attacks of specific illnesses, which illnesses can be treated prophylactically and therapeutically with the active agent melatonin.

It will be understood that each of the steps, conditions, and medical agents described above, or two or more together, may also find a useful application in other types of procedures and products differing from the types described above.

While the invention has been illustrated and described as embodied in the context of the use of melatonin for the production of a peroral pulsatile form of medication, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. Peroral pulsatile forms of medication with melatonin for safeguarding effective blood values consisting of melatonin, wherein an invasion phase of melatonin of less than two hours is employed;

and wherein, after application, the blood concentration of melatonin exhibits a first peak and a second peak spaced by a time period, and wherein a maximum of endogenous melatonin is observed in between.

2. A production of peroral pulsatile forms of medication containing melatonin comprising melatonin incorporated in pharmaceutically compatible carrier substances having different dielectric constants, wherein these carrier substances containing the active ingredient are mixed in a ratio corresponding to the required delivery of the active ingredient, and wherein the resulting mixtures of the carrier substances containing the active ingredient are formed into a pulsatile form of medication of melatonin, wherein an invasion phase of less than 2 hours is obtained.

3. The production of peroral pulsatile forms of medication containing melatonin according to claim 2, wherein the pulsatile form of medication is a capsule.

4. The production of peroral pulsatile forms of medication containing melatonin according to claim 2, wherein the mixture of melatonin and carrier substance contains from about 4 to 10 weight percent of melatonin.

5. A method for treating disorders based on improper levels of melatonin in the blood of a person, comprising mixing melatonin with a first carrier substance suitable for a relatively quick release of melatonin after oral administration resulting in a first component;

mixing melatonin with a second carrier substance suitable for a relatively slow release of melatonin after oral administration resulting in a second component;

mixing the first component and the second component to a pulsatile mixture;

forming the pulsatile mixture into a perorally administrable medication;

administering the perorally administrable medication to a patient suffering from a disorder based on improper levels of melatonin.

6. The method according to claim 5, wherein the first carrier substance is peanut oil.

7. The method according to claim 5, wherein the second carrier substance is collagen.

8. The method according to claim 5, wherein the amount of melatonin in the first mixture is from about 4 to 10 weight percent, and wherein the amount of melatonin in the second component is from about 4 to 10 weight percent.

9. The method according to claim 5, wherein the perorally administrable medication is a capsule.

10. The method according to claim 5, wherein the first carrier substance is a member of the group consisting of glycol esters of alkane acids, glycol esters of alkene acids, glycerol esters of alkane acids, glycerol esters of alkene acids, polyalcohols, peptides and mixtures thereof.

11. The method according to claim 5, wherein the second carrier substance is a member of the group consisting of glycol esters of alkane acids, glycol esters of alkene acids, glycerol esters of alkane acids, glycerol esters of alkene acids, polyalcohols, peptides and mixtures thereof.

12. The method according to claim 5, wherein the amount of melatonin employed in one of the components is such that it is to lead to a level of melatonin in the blood in a patient which is from about 0.2 to 10 times the level of melatonin in the blood to be expected in a healthy average person under comparable circumstances.

13. The method according to claim 5, wherein the amount of melatonin employed in one of the components is such that it is to lead to a level of melatonin in the blood in a patient which is from about 0.5 to 2 times the level of melatonin in the blood to be expected in a healthy average person under comparable circumstances.

14. An oral medication for curing disorders based on improper levels of melatonin in the blood of a person, comprising melatonin mixed with a first carrier substance suitable for a relatively quick release of melatonin after oral administration defining a first component;

melatonin mixed with a second carrier substance suitable for a relatively slow release of melatonin after oral administration defining a second component, wherein the first component and the second component are mixed to form a pulsatile mixture, and wherein the pulsatile mixture is formed into an orally administrable medication.

15. The oral medication according to claim 14, wherein the first carrier substance is peanut oil.

16. The oral medication according to claim 14, wherein the second carrier substance is collagen.

17. The oral medication according to claim 14, wherein the amount of melatonin in the first mixture is from about 4 to 10 weight percent, and wherein the amount of melatonin in the second component is from about 4 to 10 weight percent.

18. The oral medication according to claim 14, wherein the perorally administrable medication is a capsule.

19. The oral medication according to claim 14, wherein the first carrier substance is a member of the group consisting of glycol esters of alkane acids, glycol esters of alkene acids, glycerol esters of alkane acids, glycerol esters of alkene acids, polyalcohols, peptides and mixtures thereof.

20. The oral medication according to claim 14, wherein the second carrier substance is a member of the group consisting of glycol esters of alkane acids, glycol esters of alkene acids, glycerol esters of alkane acids, glycerol esters of alkene acids, polyalcohols, peptides and mixtures thereof.

21. Peroral pulsatile forms of medication with melatonin formed as a capsule and having an invasion phase of melatonin of less than two hours and exhibiting a release profile according to FIG. 3.

22. Peroral pulsatile bimodal medication with melatonin in the form of a capsule for assuring effective blood values of the medication with an invasion phase of less than two hours,
   wherein the medication melatonin is present in a first component and in a second component in the capsule, and
   wherein the second component is released with a delay as compared to a release of the first component;
   wherein an available concentration of the medication melatonin of the second component is identical to or lower than an available concentration of the medication melatonin of the first component.

23. A method for the production of peroral pulsatile forms of melatonin for safeguarding effective blood values of medical substances, comprising
   melatonin incorporated in a conventional way in pharmaceutically compatible carrier substances having different dielectric constants,
   wherein these carrier substances containing the active ingredient are mixed in a ratio corresponding to the required delivery of the active ingredient,
   and wherein the resulting mixture of the carrier substances containing the active ingredient is formed into a pulsatile form of medication, wherein an invasion phase of melatonin of less than two hours is employed;
   and wherein, after application, the blood concentration of melatonin exhibits a first peak and a second peak spaced by a time period, and wherein a maximum of endogenous melatonin is observed in between the first peak and the second peak.

24. The method according to claim 5, wherein the second carrier substance is collagen having embedded melatonin and wherein the microballs have a diameter of from about 30 to 100 micrometers.

* * * * *